(12) United States Patent
Avril et al.

(10) Patent No.: US 11,717,777 B2
(45) Date of Patent: Aug. 8, 2023

(54) NONWOVEN FABRIC

(71) Applicant: Don & Low Limited, Angus (GB)

(72) Inventors: David Avril, Dundee (GB); Robert Ronald Murphy, Invergowrie (GB); Lesley Ray Haynes, Angus (GB)

(73) Assignee: DON & LOW LIMITED, Angus (GB)

( * ) Notice: Subject to any disclaimer, the term of this patent is extended or adjusted under 35 U.S.C. 154(b) by 163 days.

(21) Appl. No.: 16/772,013

(22) PCT Filed: Nov. 29, 2018

(86) PCT No.: PCT/GB2018/053463
§ 371 (c)(1),
(2) Date: Jun. 11, 2020

(87) PCT Pub. No.: WO2019/116000
PCT Pub. Date: Jun. 20, 2019

(65) Prior Publication Data
US 2021/0086117 A1    Mar. 25, 2021

(30) Foreign Application Priority Data
Dec. 14, 2017 (GB) .................................. 1720899
Sep. 3, 2018 (GB) .................................. 1814285

(51) Int. Cl.
*B32B 5/22* (2006.01)
*B01D 39/16* (2006.01)
(Continued)

(52) U.S. Cl.
CPC .......... *B01D 39/1623* (2013.01); *B32B 5/022* (2013.01); *B32B 5/08* (2013.01);
(Continued)

(58) Field of Classification Search
CPC .. B32B 5/022; B32B 5/08; B32B 5/26; B32B 37/06; B32B 37/10; B32B 38/06;
(Continued)

(56) References Cited

U.S. PATENT DOCUMENTS 5,188,885 A * 2/1993 Timmons .................. B32B 5/26
128/849
5,308,691 A * 5/1994 Lim ......................... D04H 1/56
156/308.2
(Continued)

FOREIGN PATENT DOCUMENTS

EP 0370835 5/1990
EP 0416620 11/1991
(Continued)

OTHER PUBLICATIONS

International Search Report and Written Opinion for PCT/GB2018/053463 dated Feb. 13, 2019, 18 pages.
(Continued)

*Primary Examiner* — Matthew D Matzek
(74) *Attorney, Agent, or Firm* — Myers Bigel, P.A.

(57) ABSTRACT

There is disclosed a nonwoven laminate (5) or laminate fabric comprising at least three layers (10, 20) comprising spunbond/meltblown/spunbond layers, wherein the laminate (5) has: an abrasion resistance of at least 5,000 rubs or higher, and a microbiological filtration performance measured as a log reduction factor (LRF) of 3 or higher. The laminate (5) comprises a medical and/or pharmaceutical fabric such as for medical and/or sterile packaging. Beneficially the laminate (5) has been flat calendared between flat heated metal rollers (105, 110) and further, the laminate (5) has been flat calendar laminated between flat heated metal rollers (105, 110).

15 Claims, 5 Drawing Sheets

(51) Int. Cl.
  *B32B 5/02* (2006.01)
  *B32B 5/08* (2006.01)
  *B32B 5/26* (2006.01)
  *B32B 37/06* (2006.01)
  *B32B 37/10* (2006.01)
  *B32B 38/06* (2006.01)

(52) U.S. Cl.
  CPC ............... *B32B 5/26* (2013.01); *B32B 37/06* (2013.01); *B32B 37/10* (2013.01); *B32B 38/06* (2013.01); *B32B 2250/03* (2013.01); *B32B 2250/20* (2013.01); *B32B 2250/242* (2013.01); *B32B 2250/40* (2013.01); *B32B 2262/0253* (2013.01); *B32B 2262/12* (2013.01); *B32B 2307/724* (2013.01); *B32B 2439/80* (2013.01)

(58) Field of Classification Search
  CPC ............ B32B 2250/03; B32B 2250/20; B32B 2250/242; B32B 2250/40; B32B 2262/0253; B32B 2262/12; B32B 2307/724; B32B 2439/80; B32B 2307/554; B32B 2535/00; B32B 2262/14; B01D 39/1623; A61B 50/00; A61B 2017/00526
  USPC .... 442/382, 400, 401, 345; 428/36.5, 304.4, 428/311.11
  See application file for complete search history.

(56) References Cited

U.S. PATENT DOCUMENTS

| | | | |
|---|---|---|---|
| 2006/0096003 | A1 | 5/2006 | Plaatje et al. |
| 2012/0234333 | A1 | 9/2012 | Jenkins et al. |
| 2014/0155854 | A1* | 6/2014 | MacDonald ........... D04H 3/007 428/401 |
| 2014/0276517 | A1* | 9/2014 | Chester ................... A61L 15/24 442/364 |
| 2015/0275404 | A1* | 10/2015 | Erlandsson ............... D01F 8/04 442/364 |

FOREIGN PATENT DOCUMENTS

| | | | | |
|---|---|---|---|---|
| EP | 0754796 | A1 | 1/1997 | |
| EP | 2034056 | | 3/2009 | |
| GB | 2494544 | | 3/2013 | |
| GB | 2494544 | A * | 3/2013 | ............. B32B 5/022 |
| GB | 2495622 | | 4/2013 | |
| GB | 2496244 | A * | 5/2013 | ......... B32B 37/0076 |
| WO | 95/15848 | | 6/1995 | |
| WO | 97/23677 | | 7/1997 | |
| WO | 00/37723 | | 6/2000 | |
| WO | 2004/003278 | | 1/2004 | |

OTHER PUBLICATIONS

Communication for corresponding European Patent Application No. 18815798.6 dated May 19, 2021, 7 pages.
International Preliminary Report on Patentability PCT/GB2018/053463 dated Jun. 25, 2020, 11 pages.

* cited by examiner

NONWOVEN FABRIC

FIELD OF INVENTION

The present invention relates generally to fabrics such as nonwoven fabrics. The invention also relates to breathable or permeable fabrics, e.g. liquid impermeable and/or liquid vapour and/or gas permeable fabrics. The invention more particularly, though not exclusively, relates to air and/or moisture/water vapour permeable and liquid impermeable fabrics.

Fabrics according to the present invention may find particularly beneficial utility as sterile medical and/or pharmaceutical packaging fabrics, e.g. as a fabric for packaging in which medical products, devices or instruments may be contained, retained or held and/or sterilised, e.g. prior to use.

BACKGROUND OF INVENTION

According to EDANA (the European Disposables and Nonwovens Association), a 'nonwoven' is a sheet of filaments (continuous filaments), fibres or chopped yarns of any nature or origin that have been formed into a web by any means, and bonded together by any means with the exception of weaving or knitting.

Nonwovens typically have specific characteristics which can be selectably engineered dependent upon end use, e.g. moisture vapour permeability, gas/air permeability, liquid impermeability, resilience, stretch, softness, strength, flame retardancy, washability, cushioning and/or filtering.

A spunlaid nonwoven (also referred to herein as a spunbond or meltblown fabric) comprises a spunlaid web. A spunbond nonwoven material is formed of continuous filaments—typically having a filament diameter greater than 20 micron ($\mu m$). A meltblown nonwoven material is comprised of discontinuous fibres—typically having a fibre diameter greater than 2.5 micron ($\mu m$). The spunlaid web can be bonded by one or more techniques to provide fabric integrity. One such technique is point-bonding (e.g. calendar point-bonding) which typically uses heat and pressure in a predetermined discrete (point) pattern to bind thermoplastic filaments or fibres to form a (self-supporting) nonwoven fabric. The filament or fibres of nonwoven fabrics typically comprise polymers or thermoplastics, e.g. polypropylene or alternatively polyethylene or polyester.

Composite structures or "laminates" comprise layers of nonwovens, such as spunbond/meltblown/spunbond (SMS), with each nonwoven component playing a prevalent role.

Nonwoven materials can be used in breathable sterile packaging. High performance breathable medical sterile packaging (MSP) fabrics are classified by high efficiency removal of microbiological contamination in an airstream passing through the fabric.

U.S. Pat. No. 5,308,691 (DUPONT) describes controlled porosity composite sheets comprising a melt-blown polypropylene fibre web having a spunbonded polypropylene fibre sheet laminated to at least one side thereof, which are made by calendaring an assembly of the component webs. Such are suitable for making housewrap sheets and sheets for sterile packaging.

First Problem (Meltblown Embodiment)

Microbiological filtration performance can be measured as a Log Reduction Factor (LRF) of the concentration of microbes in an air stream measured both before and after passing contaminated air through an MSP fabric. A test method typically used to measure the microbiological performance of a MSP nonwoven is ASTM F1608.

A conventional meltblown nonwoven material laminated between two layers of conventional spunbond nonwoven layers can achieve an LRF value of 2.1, which is considered to be insufficient for a nonwoven to be used in high performance MSP applications. Further processing to reduce the pore size of the nonwoven laminate is not believed to improve the LRF value.

Second Problem (Spunbond Embodiment)

A key property of nonwovens for use in MSP, such as a medical pouch, is that the nonwoven does not shed fibres, particularly when the packaging is opened. Any fibre shedding could compromise the sterility and cleanliness of any item(s) contained within the packaging.

Fibre shedding of conventional nonwoven spunbond materials can be improved (i.e. decreased) by calendaring the nonwoven spunbond material. The process of flat calendaring a nonwoven spunbond, e.g. between two heated flat steel rollers, thermally consolidates the fabric. This flat calendaring consolidation process involves melting and fusing the filaments at their intersection with other filaments, reducing the extent of any fibre shedding. However, the property of fabric shedding of a conventional nonwoven spunbond material effectively reaches an optimum value which, despite additional flat calendaring, cannot be improved further. Conventional nonwoven materials for MSP have been found to show significant amounts of fibre shedding.

The present Inventors have noted that the ability of a nonwoven to potentially shed fibres is directly related to the property of abrasion resistance. Abrasion resistance of a nonwoven may be measured using EDANA NWSP 020.5 which involves subjecting a nonwoven fabric specimen to a rubbing motion under known conditions of pressure and abrasive action. Nonwoven fabric specimens are subjected to abrasive wear for a given number of rubs at a given pressure. After the abrasion test is completed the nonwoven specimens are rated according to a pictorial standard.

Measurement of fibre shedding can also be measured qualitatively. This can be determined either by sealing the nonwoven to another substrate and then peeling the layers apart and examining the other substrate to determine the amount of spunbond filaments that have separated from the nonwoven, having been left on the other substrate. Alternatively, a simpler method is to apply an adhesive tape to the nonwoven, using a roller to ensure a good bond, then removing the tape and examining the tape to see how many filaments from the nonwoven have been removed.

Third Problem (Laminate Embodiment)

Laminates of SMS nonwoven materials can be used in MSP. However, such laminates can have insufficient microbiological barrier performance (LRF values) and/or high fibre shedding.

In the art there are two steps for production of a flat calendared nonwoven laminate. Firstly, a lamination step, where nonwoven layers are combined using an embossed conventional thermal calendar roller. The resulting laminate is then flat calendared between two hot steel rollers to maximise the extent of any thermal consolidation. However, even by maximising the extent of thermal consolidation using this process route, the required level of abrasion resistance/fibre shedding or microbiological filtration performance in the resultant flat calendared laminate for application in a MSP cannot be achieved.

It is an object of at least one embodiment of at least one aspect of the present invention to obviate or at least mitigate one or more problems in the prior art.

It is an object of at least one embodiment of at least one aspect of the present invention to provide a meltblown fabric or material with a microbiological filtration performance measured as a log reduction factor suitable for use in medical packaging.

It is an object of at least one embodiment of at least one aspect of the present invention to provide a spunbond fabric or material with an abrasion resistance suitable for use in medical packaging.

It is an object of at least one embodiment of at least one aspect of the present invention to provide a nonwoven laminate fabric or material with an abrasion resistance and/or microbiological barrier performance suitable for use in sterile and/or medical packaging.

It is an object of at least one embodiment of at least one aspect of the present invention to provide a non-woven fabric, e.g. polypropylene non-woven fabric, capable of and/or adapted for steam sterilisation.

SUMMARY OF INVENTION

According to the present invention there is provided a nonwoven laminate or fabric, use of a nonwoven laminate or fabric, and/or a method of manufacture of a nonwoven laminate or fabric according to the appended claims.

First Group (Meltblown Embodiment)

According to a first aspect of the present invention there is provided a nonwoven meltblown fabric or material, such as a medical or sterile packaging fabric or material.

The meltblown material may comprise fibres. The fibres may have an average diameter in the range of 0 μm to 4 μm, for example, in the range of 0 μm to 3 μm, less than 4 μm, or less than 3 μm. Beneficially, the fibres may have a diameter or average diameter in the range of 0.5 μm to 2 μm.

The meltblown material may comprise agglomerations of fibres. The meltblown material may comprise at least 50% of fibres which are unagglomerated, at least 75% of fibres which are unagglomerated, or at least 90% of fibres which are unagglomerated.

The meltblown material may have a microbiological filtration performance measured as a log reduction factor of 3 or higher. The microbiological filtration performance measured as a log reduction factor may be 4 or higher, 5 or higher, or 6 or higher. The meltblown material may filter and/or provide filtration of microscopic organism(s).

The meltblown material may comprise pores. The pores may have a diameter or average diameter in the range of 10 μm to 30 μm, for example, in the range of 16 μm to 28 μm. Beneficially, the pores may have a diameter or average diameter in the range of 20 μm to 25 μm.

The meltblown material may comprise or substantially comprise a polymeric material(s), e.g. a thermoplastic polymer. The polymeric material may advantageously comprise polypropylene. Alternatively the polymeric material may comprise polyethylene.

The meltblown material may be formed of polymeric fibres. Optionally, each fibre may substantially comprise or consist of a single polymer or co-polymer. The meltblown material may be formed of polyolefinic fibres, such as single component or monocomponent polyolefinic fibres. As used herein, a single component fibre may be formed by extruding from a single homogeneous polymeric material. Polyolefinic fibres used in meltblown materials of embodiments of the invention may comprise or consist of a single polyolefin homopolymer, such as a polypropylene homopolymer or a polyethylene homopolymer.

The polymeric material may comprise one or more additives, e.g. selected from ultraviolet (UV) stabilisers, hydrophobic additives, flame retardants, pigments, colour pigments and/or plasticisers.

A weight per unit area (g/m$^2$) of the meltblown material may be 10 g/m$^2$ to 100 g/m$^2$, and preferably around 30 g/m$^2$.

A water hold-out (hydrostatic head) of the meltblown material may be 15 cm to 200 cm, and preferably around 140 cm.

A moisture vapour transmission rate (MVTR) of the nonwoven material may be around 1000 g/m$^2$/24 hr.

Air permeability of the meltblown material (e.g. 30 g/m$^2$ meltblown fabric) tested to EDANA NWSP.070.1 may be 100 l/m$^2$/second to 400 l/m$^2$/second. The air permeability of the meltblown material may be less than 150l/m$^2$/second.

A thickness of the nonwoven material (e.g. 30 g/m$^2$ meltblown material) may be in the range of around 0.3 mm to 0.7 mm, e.g. 0.5 mm.

The meltblown material may be at least partially permeable and/or transparent to sterilisation means or agents, e.g. steam or ethylene oxide (EtO), electron beam, x-ray, or gamma radiation. A meltblown material made of polypropylene may be at least partially permeable and/or transparent to at least one of steam and/or ethylene oxide (EtO). The meltblown material may allow sterilisation agents to pass through the meltblown material.

The nonwoven material may be at least partially microscopic organism(s) impermeable.

The meltblown material may be gas and/or air and/or liquid/moisture vapour permeable and/or liquid/moisture impermeable.

According to a second aspect of the present invention there is provided a method of manufacturing a nonwoven meltblown fabric or material, such as a medical or sterile packaging fabric or material, of the first aspect of the present invention.

The method may comprise meltblowing a molten material. The method may comprise extruding a molten material through a die into an airstream, and collecting the material on a belt, such as a conveyor belt. The method may comprise extruding a molten material from a polymer feed through a die with a plurality of filament spinners. The method may comprise extruding the molten material into an airstream, producing a plurality of fibres. The plurality of fibres may form a web, which may be collected on a conveyor belt. The web may be thermally calendared producing the meltblown material. The meltblown material may be collected, for example, on a winder.

The die may be heated to a temperature in the range of around 250° C. to 285° C. The die may be heated to a temperature in the range of around 250° C. to 280° C., such as over 270° C., for example, around 275° C.

The airstream may be heated to a temperature in the range of around 230° C. to 300° C., such as over 290° C., for example, around 295° C.

The process air volume may be in the range of around 1100 m$^3$/hr to 2900 m$^3$/hr, for example, 1800 m$^3$/hr.

The temperature of the molten material at the nozzle of the die may be in the range of around 220° C. to 280° C., such as over 258° C., for example, around 268° C.

The material throughput may be in the range of around 25 kg/hr to 120 kg/hr, such as less than 100 kg/hour, for example, around 40 kg/hour. The material throughput may be adjusted to give an appropriate polymer throughput through each hole of the die.

The distance from the die to the collector belt may be in the range of around 100 mm to 600 mm, such as less than 220 mm, for example, around 170 mm.

Suction may be applied through the belt to collect the extruded fibres on the belt. From around 10% to 100% of the collector area on the belt may have suction applied through it. Over 55% of the collector area on the belt may have suction applied through it, for example, around at least 95% of the collector area on the belt may have suction applied through it.

The method may comprise laminating the meltblown material to at least one other layer. The method may comprise calendaring the meltblown material. The method may comprise laminating and/or calendaring the meltblown material with a calendar comprising flat rollers (or bowls) e.g. a pair of flat rollers.

By flat is or may be meant that the rollers are non-patterned and/or non-embossed. Herein by "flat" is meant to include polished and/or matt and/or sand blasted (e.g. to provide a rough engraving), e.g. to a roughness value of 30 µm to 45 µm) surface finishes to the rollers.

Second Group (Spunbond Embodiment)

According to a third aspect of the present invention there is provided a nonwoven spunbond fabric or material, such as a medical or sterile packaging fabric or material.

The spunbond material may comprise filaments. The filaments may have a diameter or average diameter less than 19 µm. Beneficially, the filaments may have a diameter or average diameter in the range of 10 µm to 19 µm, for example, 15 µm to 19 µm.

The spunbond material when flat calendar laminated may have an abrasion resistance of at least 5,000 rubs or higher. The spunbond material may have an abrasion resistance of at least 10,000 rubs or higher. The abrasion resistance of the spunbond material may be measured using EDANA NWSP 020.5 RO at 9 kPa. The abrasion resistance may be the number of rubs before fibre piling occurs.

The spunbond material may be self supporting.

The spunbond material may be point-bonded or embossed, e.g. calendar point-bonded.

An embossed area of the surface of the spunbond material may be in the range 7% to 35%, e.g. 15% to 25%, e.g. around 19% of the total surface area.

The emboss points may preferably be of diamond shape, square shape, or round shape, e.g. circular, oval or elliptical.

The emboss points may be uniformly distributed on the spunbond material, e.g. in a repeating pattern.

The spunbond material may comprise or substantially comprise a polymeric material(s), e.g. a thermoplastic polymer. The polymeric material may advantageously comprise polypropylene. The polymeric material may comprise metallocene polymer/polypropylene, such as metallocene catalysed polymer/polypropylene. Alternatively the polymeric material may comprise polyethylene.

The spunbond material may be formed of polymeric filaments. Optionally, each filament may substantially comprise or consist of a single polymer or co-polymer. The spunbond material may be formed of polyolefinic filaments, such as single component or monocomponent polyolefinic filaments. As used herein, a single component filament may be formed by extruding from a single homogeneous polymeric material. The polymeric filaments may have a melting point of less than 165° C., for example, around 151° C. Polyolefinic filaments used in spunbond materials of embodiments of the invention may comprise or consist of a single polyolefin homopolymer, such as a polypropylene homopolymer or a polyethylene homopolymer.

The spunbond material may comprise core-sheath filaments. The core-sheath filaments may comprise a core material and a sheath material. The core material and sheath material may comprise the same material in different forms (e.g. the same material with different melting points and/or rheology) or the core material may be a different material to the sheath material.

The polymeric material may comprise one or more additives, e.g. selected from ultraviolet (UV) stabilisers, hydrophobic additives, flame retardants, pigments, colour pigments and/or plasticisers.

A weight per unit area (g/m$^2$) of the spunbond material may be in the range of 15 g/m$^2$ to 100 g/m$^2$, and preferably around 35 g/m$^2$.

A moisture vapour transmission rate (MVTR) of the spunbond material may be in the range of around 1000 g/m$^2$/24 hr.

Air permeability of the spunbond material measured by EDANA NWSP.070.1 (e.g. 35 g/m$^2$ spunbond fabric) may be in the range of 720 l/m$^2$/second to 8800l/m$^2$/second, e.g. around 2600l/m$^2$/second.

A thickness of the spunbond material (e.g. 35 g/m$^2$ spunbond material) may be around 0.2 mm to 0.7 mm, e.g. around 0.4 mm.

The spunbond material may be at least partially permeable and/or transparent to sterilisation means or agents, such as steam, electron beam, or gamma radiation.

The spunbond material may allow sterilisation means to pass through the spunbond material.

The spunbond material may be at least partially microscopic organism impermeable.

The spunbond material may be gas and/or air and/or liquid/moisture vapour permeable and/or liquid/moisture impermeable.

According to a fourth aspect of the present invention there is provided a method of manufacturing a nonwoven spunbond fabric or material, such as a medical or sterile packaging fabric or material, of the third aspect of the present invention.

The method may comprise spinbonding a molten material. The method may comprise extruding a molten material through a die and collecting the material on a belt, such as a conveyor belt. The extruded material may be drawn on to the belt. The method may comprise extruding a molten material from a polymer feed through a die with a plurality of filament spinners with an extruder, producing a plurality of filaments. The plurality of filaments may form a web, which may be collected on a conveyor belt. The web may be calendared between an embossing calendar and a flat roller of a calendar, producing the spunbond material. The spunbond material may be collected on a flat roller.

The die may be heated to a temperature over 240° C., for example, around 245° C.

The temperature of the molten material at the nozzle of the die may be over 240° C., for example, around 246° C.

The material throughput may be less than 900 kg/hour, for example, around 320 kg/hour.

The method may comprise laminating the spunbond material to at least one other layer. The method may comprise calendaring the spunbond material. The method may comprise laminating and/or calendaring the spunbond material with a calendar comprising flat rollers (or bowls) e.g. a pair of flat rollers.

By flat is or may be meant that the rollers are non-patterned and/or non-embossed. Herein by "flat" is meant to include polished and/or matt and/or sand blasted (e.g. to provide a rough engraving), e.g. to a roughness value of 30 µm to 45 µm) surface finishes to the rollers.

Third Group (Laminate Embodiment)

According to a fifth aspect of the present invention there is provided a laminate or laminate material, such as a medical or sterile packaging laminate or laminate material, the laminate or laminate material comprising a nonwoven meltblown material, such as of the first aspect of the present invention, and/or a nonwoven spunbond material, such as of the third aspect of the present invention.

The laminate may comprise a nonwoven laminate, which may comprise at least three layers. The three layers may comprise spunbond/meltblown/spunbond layers. The spunbond layers may comprise respective outer layers of the laminate.

All layers of the laminate material may be nonwoven materials. The laminate material may comprise a meltblown material of the first aspect of the present invention laminated to a spunbond material of the third aspect of the present invention. The laminate may comprise a two-layer spunbound/meltblown laminate or preferably a three-layer spunbond/meltblown/spunbond laminate.

The laminate may comprise three layers. The outermost layers of the laminate may comprise a same material or at least same type of material. The laminate and/or layers of the laminate may have a spunbond/meltblown/spunbond structure or configuration.

The laminate may have an abrasion resistance of at least 5,000 rubs or higher. The laminate may have an abrasion resistance of at least 10,000 rubs or higher. The laminate may have an abrasion resistance of around 25,000 rubs. The abrasion resistance of the nonwoven may be measured using EDANA NWSP 020.5

The laminate may have a microbiological filtration performance measured as a log reduction factor of 3 or higher. The microbiological filtration performance measured as a log reduction factor may be 4 or higher, 5 or higher, or 6 or higher. The laminate may filter and/or provide filtration of microscopic organism(s).

The laminate may be at least partially permeable and/or transparent to at least one sterilisation means or agents, such as at least one of steam, ethylene oxide (EtO), electron beam, or gamma radiation and/or x-ray. A laminate made of polypropylene may be at least partially permeable and/or transparent to at least one of steam and/or ethylene oxide (EtO). The laminate may allow sterilisation means to pass through the laminate. It has been found that a laminate made of polypropylene may be of particular benefit in allowing for steam sterilisation, e.g. as compared to a laminate made of polyethylene. Each of the layers of the laminate may be made from polypropylene.

The laminate may be at least partially impermeable to microscopic organism(s).

The laminate may be gas and/or air and/or liquid/moisture vapour permeable and/or liquid/moisture impermeable.

Air permeability of the laminate measured by the Bendtsen method may be less than 670 ml/min, for example, around 60 ml/min or around 55 ml/min. Air permeability of the laminate measured by the Bendtsen method may be around 600 ml/min.

Air resistance of the laminate material measured by the Gurley method may be more than 40 s, for example, around 210 s.

The laminate may comprise pores. The pore diameter may be less than 12 µm, for example, less than 6 µm.

The meltblown layer of the laminate may comprise polymeric fibres. The polymeric fibres of the meltblown layer may comprise a single polyolefin homopolymer, such as a polypropylene homopolymer or a polyethylene homopolymer. The fibres of the meltblown layer may have an average diameter in the range of 0.5 µm to 2 µm. The meltblown layer may comprise agglomerations of fibres. The meltblown layer may comprise pores which may have a diameter or average diameter in the range of 10 µm to 30 µm.

The spunbond layers of the laminate may comprise polymeric filaments. The polymeric filaments of the spunbond layers may comprise metallocene polymer/polypropylene, such as metallocene catalysed polymer/polypropylene. The polymeric filaments of the spunbond layers may comprise core-sheath filaments. The filaments of the spunbond layers may have a diameter or average diameter less than 19 µm.

The laminate may have any of the properties of any of the layers of the laminate. For example, the laminate may comprise a meltblown material of the first aspect of the present invention, and the laminate may comprise any of the features of the first aspect of the present invention. Additionally or alternatively, the laminate may comprise a spunbond material of the third aspect of the present invention, and the laminate may comprise any of the features of the third aspect of the present invention.

The laminate may comprise at least one other material which may be selected from one or more of: a film, a woven material, a reflective (e.g. heat/IR reflective) material or film, a reinforcing net, a spunbond material and/or another nonwoven material.

Layers of the laminate may be thermally laminated to one another. The layers of the laminate may be thermally compatible, e.g. have similar melting or softening points. In this way the layers may be autogenously bonded.

According to a sixth aspect of the present invention there is provided a method of manufacturing a laminate or laminate material of the fifth aspect of the present invention.

The method may comprise laminating together at least one nonwoven material or layer and at least one other layer using a calendar comprising flat rollers (or bowls) e.g. a pair of flat rollers. The method may comprise laminating together at least one nonwoven material or layer and at least one other layer using point-bonding or embossing, e.g. calendar point-bonding. The method may comprise laminating spunbond/meltblown/spunbond layers together. The method may comprise laminating spunbond/meltblown/spunbond layers together between flat rollers, such as flat heated metal rollers.

The method may comprise laminating layers together in two or more steps. The first step may comprise laminating together at least one nonwoven material or layer and at least one other layer using a calendar comprising flat rollers or embossed rollers. The second step may comprise laminating together the laminated layers from the first step and at least one other layer using a calendar comprising flat rollers or embossed rollers.

The method may comprise calendaring the laminate with a calendar comprising flat rollers (or bowls) e.g. a pair of flat rollers, e.g. a pair of flat heated metal rollers.

By flat is or may be meant that the rollers are non-patterned and/or non-embossed. Herein by "flat" is meant to include polished and/or matt and/or sand blasted (e.g. to provide a rough engraving, e.g. to a roughness value of 30 μm to 45 μm) surface finishes to the rollers. The flat rollers may be different to one another. For example, one of the flat rollers may be smooth or polished, and the other of the flat rollers may have a roughness value of 30 μm to 45 μm.

The plurality of layers and/or the laminate may then be additionally passed through a pair of flat rollers with a nip there between. The second step of calendaring the laminate may be performed more than once. For multiple calendaring steps, the conditions of the calendaring may be the same for each calendaring step, or at least some of the steps of calendaring the laminate may have different conditions to other calendaring steps.

Preferably heat or pressure or preferably both are applied to the plurality of layers and/or the laminate passing through the nip. As the rollers are flat, the pressure and/or temperature applied to the plurality of layers and/or the laminate will be substantially uniform or even across a width of the plurality of layers and/or the laminate.

Advantageously, at least one or preferably each of the flat rollers may comprise a metal roller such as a steel roller.

Advantageously at least one or preferably each roller is heated or is provided with heating means.

Preferably the step of laminating the plurality of layers is performed "on-line", e.g. at least one of the layers, such as the nonwoven layer, is manufactured on the same line as the lamination of the plurality of layers. Alternatively, the step of laminating the plurality of layers may be performed "off-line".

Preferably the step of calendaring the laminate is performed "off-line". Alternatively, the step of calendaring the laminate may be performed "on-line".

The steps of laminating and calendaring may be performed with the same flat rollers, or may be performed with different flat rollers. The steps of laminating and calendaring may be performed under the same conditions, e.g. the pressure and/or temperature of the flat rollers may be the same for both steps. Alternatively, the steps laminating and calendaring may be performed under different conditions.

A pressure of 20 N/mm to 150 N/mm, and preferably around 100 N/mm, may be applied to the plurality of layers during the lamination between the rollers.

A temperature of 90° C. to 170° C., and preferably around 135° C., may be applied to the plurality of layers during the lamination between the rollers.

A pressure of 20 N/mm to 150 N/mm, and preferably around 130 N/mm, may be applied to the laminate during calendaring between the flat calendar rollers.

A temperature of 90° C. to 170° C., and preferably around 154° C., may be applied to the laminate during calendaring between the flat calendar rollers.

The speed of the first pass may be in the range of 10 m/min to 25 m/min, preferably around 10 m/min.

The speed of the second pass may be in the range of 5 m/min to 15 m/min, preferably around 7.5 m/min.

It will be appreciated that any of the features, e.g. optional features, of any of the foregoing aspects of the present invention may be used in any of the other aspects of the present invention whether alone or in combination, and are not recited herein in full merely for reasons of brevity.

BRIEF DESCRIPTIONS OF DRAWINGS

Embodiments of the present invention will now be described by way of example only, and with reference to the accompanying drawings, which are.

DETAILED DESCRIPTION OF DRAWINGS

First Embodiment (Meltblown)

Figure 1:
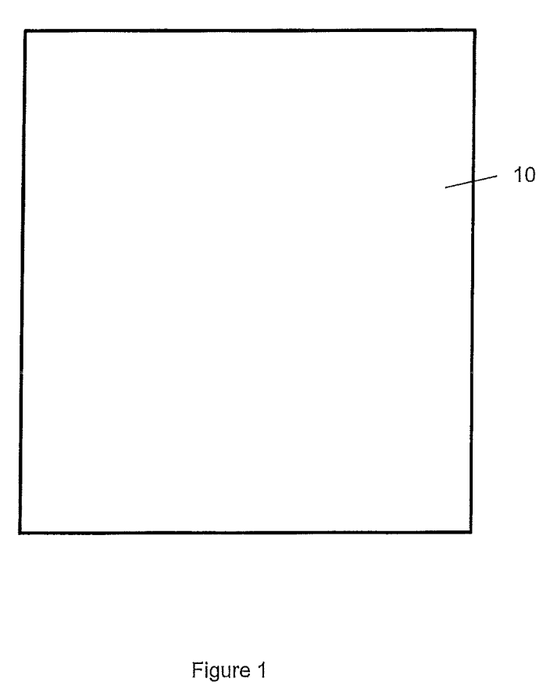
FIG. 1 a meltblown fabric according to a first embodiment of the present invention.

Referring initially to FIG. 1, according to a first embodiment of the present invention there is provided a meltblown fabric or material 10, such as a medical or sterile packaging fabric or material.

The meltblown material 10 comprises fibres. The fibres have an average diameter in the range of 0.5 μm to 2 μm. The laminate containing the meltblown material 10 has a microbiological filtration performance measured as a log reduction factor of 3 or higher. The meltblown material 10 filters microscopic organism(s). The un-calendared meltblown material 10 comprises pores. The pores have a diameter or average diameter in the range of 20 μm to 25 μm. The meltblown material 10 comprises a polymeric material(s), e.g. a thermoplastic polymer. The meltblown material 10 is formed of polymeric fibres, and each fibre comprises a single polymer. The meltblown material 10 is, in this embodiment, formed of single component polypropylene homopolymer.

The weight per unit area ($g/m^2$) of the meltblown material 10 in this embodiment is around 30 $g/m^2$. The water hold-out (hydrostatic head) of the meltblown material 10 in this embodiment is around 140 cm. The air permeability of the meltblown material 10 (e.g. 30 $g/m^2$ meltblown fabric) is less than 150 $I/m^2$/second.

The meltblown material 10 is at least partially permeable and/or transparent to sterilisation means or agents, in this embodiment, steam, and/or ethylene oxide (EtO). Electron beam, or gamma radiation would degrade the polypropylene used in this embodiment. The meltblown material 10 allows sterilisation means to pass through the meltblown material. The meltblown material 10 is gas and air and liquid/moisture vapour permeable and liquid/moisture impermeable.

Figure 2:
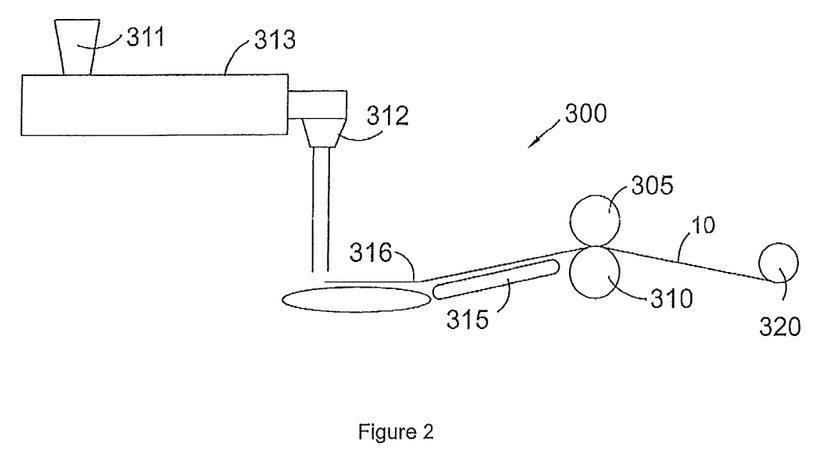
FIG. 2 a schematic diagram of an apparatus for manufacture of the meltblown fabric of FIG. 1.

Referring to FIG. 2, there is shown an apparatus, generally designated 300 for use in a method of manufacturing the meltblown fabric 10

The method comprises meltblowing a molten material with an apparatus 300. The method comprises extruding a molten material from a polymer feed 311 through an extruder 313, then through a die with a plurality of spinnerets 312 into an airstream, producing a plurality of fibres. The plurality of fibres form a web 316, which is collected on a conveyor belt 315. The meltblown material is calendared between rollers 305 and 310, and is collected on a winder 320.

The die is heated to a temperature of 275° C. The airstream is heated to a temperature of 295° C. The process air volume is 1800 $m^3$/hr. The temperature of the molten polymer material at the nozzle of the die is around 268° C.

The material throughput in this embodiment is 40 kg/hour. The distance from the die to the conveyor belt 315 in this embodiment 170 mm.

Suction is applied through the conveyor belt 315 to collect the extruded fibres on the belt. In this embodiment around 95% of the collector area on the conveyor belt 315 has suction applied through it.

Second Embodiment (Spunbond)

Figure 3A:
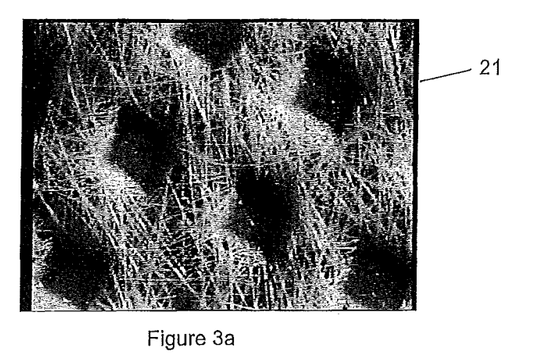
FIGS. 3a and b a spunbond fabric of the art; and a spunbond fabric according to a second embodiment of the present invention, respectively.
Figure 3B:
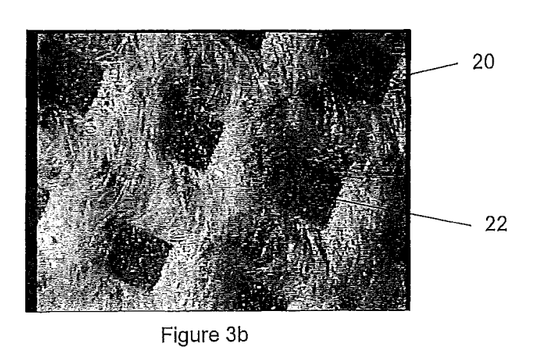

Referring to FIG. 3b, according to a second embodiment of the present invention there is provided a spunbond fabric or material 20, The spunbond material 20 comprises filaments. In this embodiment, the filaments have a diameter or average diameter in the range of 15 µm to 19 µm. The filaments of the spunbond material 20 have a smaller diameter or average diameter than the filaments of the spunbond material of the art 21 (see FIG. 3a).

The spunbond material 20 has an abrasion resistance of 10,000 rubs or higher. The spunbond material 20 is self-supporting. The spunbond material 20 is point-bonded or embossed, e.g. calendar point-bonded 22. The embossed area of the surface of the spunbond material in this embodiment around 19% of the total surface area. The emboss points 22 are uniformly distributed on the spunbond material 20 in a repeating pattern.

The spunbond material 20 is formed of polymeric filaments, and each filament comprises a single polymer. The spunbond material 20 is formed of single component metallocene catalysed polypropylene homopolymer.

The weight per unit area (g/m$^2$) of the spunbond material 20 in this embodiment is around 35 g/m$^2$.

The spunbond material 20 is at least partially permeable and/or transparent to sterilisation means or agents 50, such as steam, and ethylene oxide (EtO). The spunbond material 20 allows sterilisation means 50 to pass through the spunbond material 20.

Figure 4:
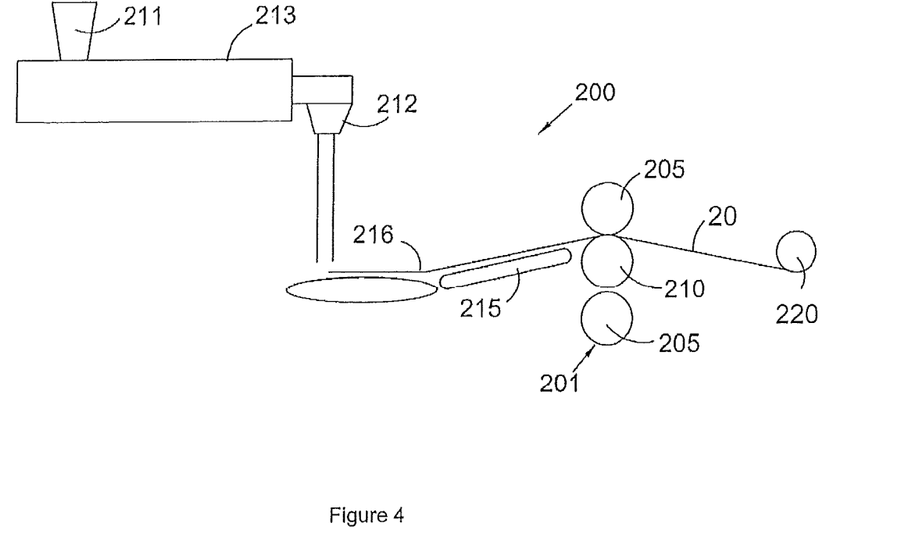
FIG. 4 a schematic diagram of an apparatus for manufacture of the spunbond fabric of FIG. 3b.

Referring to FIG. 4, there is shown an apparatus, generally designated 200 for use in a method of manufacturing the spunbond fabric or material 20.

The method of manufacturing the spunbond material 20 comprises melt spinning a molten material with an apparatus 200. The method comprises extruding a molten polymer from a polymer feed 211 through an extruder 213, then a die with a plurality of filament spinnerets 212, producing a plurality of filaments. The plurality of filaments form a web 216, which is collected on a conveyor belt 215. The web 216 is calendared between an embossing calendar 205 and a flat roller 210 of a calendar 201, producing the spunbond material 20. The spunbond material 20 is collected on a winder 220.

The die is heated to a temperature in this embodiment of 245° C. The temperature of the molten material at the nozzle of the die in this embodiment is 246° C. The material throughput in this embodiment is 320 kg/hour.

Third Embodiment (Laminate)

Figure 5:
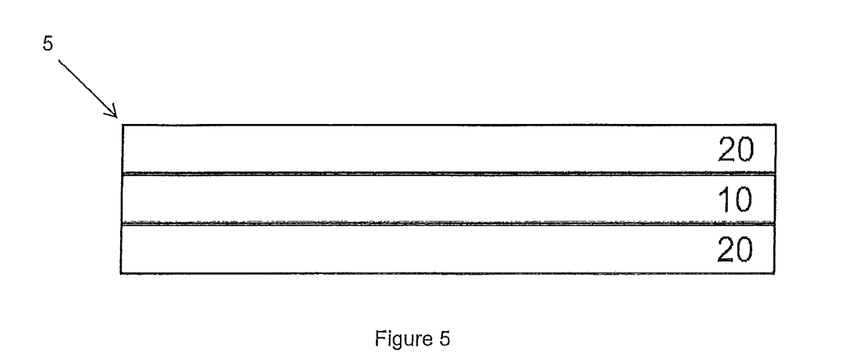
FIG. 5 a laminate according to a third embodiment of the present invention.

Referring to FIG. 5, according to a third embodiment of the present invention there is provided a laminate 5, such as a medical or sterile packaging laminate material, the laminate 5 comprising the meltblown material 10, and the further spunbond material 20, for example, of the first and second embodiments of the present invention, respectively.

The layers of the laminate material 5 are nonwoven materials 10, 20. The laminate material 5 comprises a meltblown material 10 of the first aspect/first embodiment of the present invention laminated between spunbond materials 20 of the third aspect/second embodiment of the present invention.

The laminate 5 comprises three layers. The outermost layers of the laminate 5 comprise the same material 20. The layers of the laminate 5, therefore, have a spunbond/meltblown/spunbond structure or configuration.

The SMS laminate 5, when (subsequently) flat calendared, has an abrasion resistance of 10,000 rubs or higher. The abrasion resistance of the nonwoven is measured using EDANA NWSP 020.5 RO.

The SMS laminate when (subsequently) flat calendared has a microbiological filtration performance measured as a log reduction factor of 4 or higher. The laminate 5 filters microscopic organism(s).

The laminate 5 is at least partially permeable and/or transparent to at least one sterilisation means or agents 50, such as at least one of steam and ethylene oxide (EtO). The laminate 5 allows sterilisation means to pass through the laminate 5. The laminate 5 is at least partially microscopic organisms impermeable. The laminate 5 is gas and/or air and/or liquid/moisture vapour permeable and/or liquid/moisture impermeable.

The laminate 5 has the properties of the layers of the laminate 5. In this embodiment, the laminate 5 comprises the features of the first aspect of the present invention, by incorporation of a meltblown material 10 of the first aspect/first embodiment of the present invention in the laminate 5. The laminate 5 similarly has the features of the spunbond material 20 of the third aspect/second embodiment of the present invention.

Layers of the laminate 5 are thermally laminated to one another between flat calendar rollers. The layers of the laminate 5 are thermally compatible; in this embodiment the layers of the laminate 5 have similar melting or softening points. In this way the layers are autogenously bonded.

Figure 6:
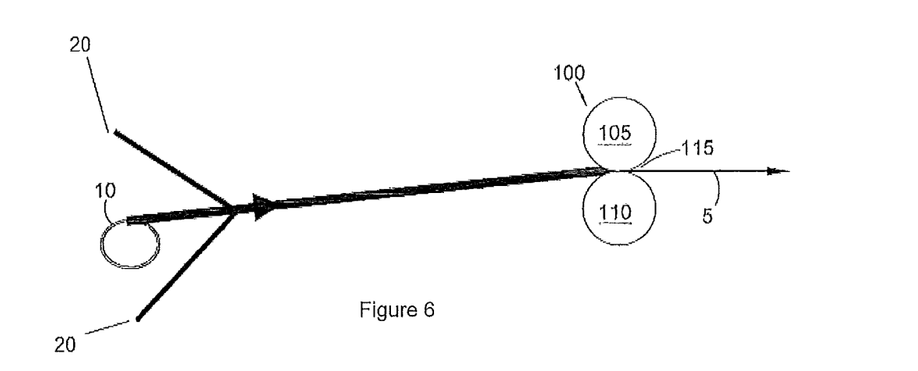
FIG. 6 a schematic diagram of an apparatus for manufacture of the laminate of FIG. 5.

Referring to FIG. 6, according to an embodiment of the present invention, there is provided a method of manufacturing the laminate 5 comprising:

step 1—laminating together one nonwoven layer 10 and two other nonwoven layers 20 using a calendar 100 comprising flat rollers (or bowls) e.g. a pair of flat (heated) rollers 105, 110; and step 2—calendaring the resulting laminate 5 with a calendar comprising flat rollers (or bowls) e.g. a/the pair of flat rollers 105, 110.

By flat it is meant that the rollers 105, 110 are non-patterned and/or non-embossed. Herein by "flat" is meant to include polished and/or matt and/or sand blasted (e.g. to provide a rough engraving, in this embodiment to a roughness value of 30 µm to 45 µm) surface finishes to the rollers.

The plurality of layers 10, 20 and/or the laminate 5 are passed through a pair of flat rollers 105, 110 with a nip 115 therebetween.

Both heat and pressure are applied to the plurality of layers 10, 20 and the laminate 5 passing through the nip 115. As the rollers 105, 110 are flat, the pressure and temperature applied to the plurality of layers 10, 20 and the laminate 5 are substantially uniform across the width of the plurality of layers 10, 20 and the laminate 5.

Each of the flat rollers 105, 110 comprises a steel roller, and each roller 105, 110 is provided with heating means.

In this example the step of laminating the plurality of layers 10, 20 is performed "off-line", i.e. in this embodiment the step of laminating the plurality of layers 10, 20 is not done on apparatus 200. It is, therefore, laminated on apparatus 100.

The step of calendaring the laminate 5 is performed "off-line". The steps of laminating and calendaring are performed with the same flat rollers 105, 110. The steps of laminating and calendaring are performed under different conditions.

A pressure of 100 N/mm is applied to the plurality of layers 10, 20 during the lamination between the flat calendar rollers 105, 110. A temperature of 135° C. is applied to the plurality of layers 10, 20 during the lamination between the flat calendar rollers 105, 110.

A pressure of 130 N/mm is applied to the laminate 5 during the calendaring between the flat calendar rollers 105, 110. A temperature of 154° C. is applied to the laminate 5 during the calendaring between the flat calendar rollers 105, 110.

The speed of the first pass is 10 m/min. The speed of the second pass is 7.5 m/min.

EXAMPLES

Examples of the present invention will now be given.

Example 1 (Fine Fibred Meltblown)

Table 1 below compares standard processing parameters for manufacturing a meltblown fibre with the processing properties for manufacturing a meltblown fabric according to an embodiment of the present invention.

TABLE 1

Meltblown Process Conditions

|  | Standard process parameters | Process parameters of the present invention |
|---|---|---|
| Die Temperature (° C.) | 270 | 275 |
| Process Air Set Temperature (° C.) | 290 | 295 |
| Process Air Volume (%) | 55 | 62 |
| Nozzle Melt Temperature (° C.) | 258 | 268 |
| Suction Zone 2 (%) | 55 | 95 |
| Polymer throughput (kg/hour) | 100 | 40 |
| Die to Collection Belt Distance DCD (mm) | 220 | 170 |

It has been discovered that finer fibred polypropylene meltblown can be achieved with the meltblown process through changes to process settings that result in: (i) reduced polymer throughput per hole of the die, (ii) increased air speed at the die to increase draw on the polymer, (iii) increased polymer temperature to reduce viscosity and hence increase ability to increase attenuation of fibres, and (iv) less fibre entanglement.

(i) Reduced polymer throughput per hole of the die—reduction in throughput (mass) of polymer passing through each die hole yields a reduction in the diameter of the resultant fibre produced. This reduction in polymer throughput means that there is less polymer to draw (attenuate) resulting in a finer fibre. It has been discovered that a reduction of 60% throughput yields the finest fibre whilst maintaining process integrity.

(ii) Increased air speed at the die to increase draw on the polymer—process air is the air directed at molten polymer leaving the die. Increasing process air flow rate increases attenuation of the fibre. Increased process air flow also increases fibre velocity and thus reduces fibre travel time to the collection belt. Because it takes time for fibre entanglement to occur (resulting in coarse fibre agglomerations (bundles)), any process change that decreases fibre travel time reduces fibre entanglement, thus decreasing the number of coarse fibre agglomerations (bundles).

(iii) Increased polymer temperature to reduce viscosity—increasing melt temperature through an increase in extruder, die, and process air temperature results in lower material viscosity: allowing material to flow more easily and for fibres to attenuate further.

(iv) Less fibre entanglement—fibres commonly become entangled during processing into tight fibre agglomerations (bundles); these may be composed of single fibres or a large number of fibres. When fibre entanglement is reduced, the number and size of agglomerations (bundles) is reduced. Reducing the DCD (Die to Collection belt Distance) has the effect by reducing fibre travel time to the collection belt, which reduces coarse fibre agglomerations (bundles), for the reasons described above.

Suction onto the collection belt is also increased to address the problem of fibre fly during production. Due to the low mass of these fibres, they are likely to be blown off the collection belt before having time to stick and crystallise. Greater belt suction applies more downward force on the fibres to encourage these finer fibres to be drawn to and remain on the belt.

Table 2 below compares the properties of meltblown fibres made by the standard method with the properties of meltblown fibres of an embodiment of the present invention.

TABLE 2

Meltblown Properties

| | Area weight g/m$^2$ | Fibre diameter (μm) | Air Permeability l/m$^2$/second (EDANA NWSP.070.1) | Pore diameter (μm BS3321) |
|---|---|---|---|---|
| Conventional Polypropylene Meltblown | 30 | 2.53 | 237 | 34 |
| 'Fine Fibred' Polypropylene meltblown | 30 | 1.24 | 131 | 22 |

It has been found that the microbiological barrier performance (measured as LRF) of the spunbond/meltblown/spunbond (SMS) laminate can be positively influenced by reducing the fibre diameter of the meltblown layer used. The finer fibred meltblown layer yields a lower pore size.

This lower pore size, created by using the finer fibred meltblown, yields a much higher microbiological barrier performance, whilst retaining fabric breathability. Surprisingly LRF values of up to 6.1 have been obtained in laminates incorporating this finer fibred meltblown fabric.

Such a meltblown material can be used as the inner layer in a spunbond/meltblown/spunbond (SMS) structure nonwoven laminate. Table 3 below compares the properties of a SMS laminate made with conventional meltblown layer and conventional spunbond layer with the properties of a SMS laminate made with a meltblown layer and spunbond layer both according to the present invention. The meltblown layer in each laminate is 30 gsm.

TABLE 3

| | Meltblown weight g/m² (incorporated into laminate) | Fibre diameter (μm) | Air Permeability (ml/min) (Bendtsen method ISO 5636-3) | Pore diameter (μm BS3321) | Microbiological Barrier Performance (Log Reduction Factor) ASTM F1608 |
|---|---|---|---|---|---|
| Conventional Polypropylene Meltblown | 30 | 2.53 | 60 | 12 | 3.1 |
| 'Fine Fibred' Polypropylene Meltblown | 30 | 1.24 | 55 | <12 | 4.6 |

Example 2 (Fine Fibred Metallocene Spunbond)

The abrasion resistance/fibre shedding properties of a spunbond fabric can be improved by increasing the extent of filament/filament bonding by decreasing filament diameter. This increases the length of filament for a given weight of fabric, and hence increases the number of filament/filament intersections that can be bonded. Increasing the number of filament/filament bond points results in a considerable increase in abrasion resistance (over 2 orders of magnitude increase), with a resultant decrease in fibre shedding.

The filament diameter of spunbond filaments produced using conventional polypropylene homopolymer cannot be decreased beyond a certain point—due to filament breaking when trying to increase the draw on molten polypropylene polymer during extrusion, i.e. the filament diameter is restricted by the rheology of the polypropylene polymer as the rheology dictates the melt strength of the polymer during extrusion. The stronger the melt strength on the molten polymer, the greater draw one can apply, and hence the finer filaments that can be produced.

Producing spunbond using metallocene, controlled rheology, polypropylene polymer allows increased draw during extrusion due to higher strength of this polymer in its molten state. By combining a lower throughput through each spinneret hole, combined with higher draw results in the production of finer fibres.

Decreasing filament diameter using metallocene polypropylene has a number of positive impacts on the abrasion performance, and hence improvement in fibre shedding, for example:

the lower melting point of metallocene polypropylene spunbond increases the degree of thermal consolidation for a given thermal calendar setting (temperature, pressure and throughput), hence improved bonding at the filament/filament intersection is observed;

finer filaments have physically less mass to melt, during the thermal calendaring process, at filament/filament intersection, hence improving bonding;

finer filaments mean that for a given weight of fabric there are considerably more filaments per unit area hence there are considerably more filament/filament intersections, giving more thermal bond points and hence improved abrasion resistance and significantly reduced fibre shedding;

when incorporated into a spunbond/meltblown/spunbond laminate, the lower melting point of the outer spunbond layers (produced using metallocene polypropylene) is better able to bond to the other layers of the laminate. Hence the individual layers of the laminate are more firmly bonded together and less liable to delaminate when peeled away from another substrate to which it is bonded. This better laminate integrity also reduces the amount of fibre shedding as the individual layers of the laminate are less liable to peel apart.

An improvement in abrasion resistance from 100 rubs (before fabric pilling occurred) to greater than 10,000 rubs has been found. This dramatic improvement in abrasion resistance effectively eliminates fibre shedding when the fabric is peeled from another substrate. Such a spunbond material can be used as the outer layers in a spunbond/meltblown/spunbond (SMS) structure nonwoven laminate. Table 4 below compares properties of SMS laminates not according to the invention (Comparative Example Sample A and Example Sample B) with one according to the present invention (Embodiment Sample C). Table 4 compares the properties of SMS laminates made with conventional spunbond layers and fine fibred meltblowns with the properties of an SMS laminate made with spunbond layers and with fine fibred meltblown according to the present invention. The laminate of the invention was laminated between flat rollers and subsequently flat calendared.

TABLE 4

| Spunbond Polymer | Spunbond Melt Point °C. | Filament Diameter μm BS3321 | Calender Conditions | Abrasion Resistance EDANA NWSP 020.5.RO | Fibre Shedding |
|---|---|---|---|---|---|
| Sample A: Conventional Polypropylene Homopolymer | 163 | Average 20.87 Range 19.5-23.5 | Embossed Bowl 136° C. Smooth Bowl 166° C. Pressure 32 N/mm | 800 rubs | Considerable |

TABLE 4-continued

| Spunbond Polymer | Spunbond Melt Point °C. | Filament Diameter μm BS3321 | Calender Conditions | Abrasion Resistance EDANA NWSP 020.5.RO | Fibre Shedding |
|---|---|---|---|---|---|
| Sample B: Conventional Polypropylene Homopolymer | 163 | Average 20.87 Range 19.5-23.5 | Flat Bowl 147° C. Smooth Bowl 147° C. Pressure 100 N/mm | 100 rubs | Considerable |
| Sample C: Metallocene Polypropylene | 151 | Average 16.98 Range 15.0-18.5 | Flat Bowl 154° C. Smooth Bowl 154° C. Pressure 130 N/mm | >10,000 rubs | None |

10,000 rub abrasion resistance is consistent with other medical packaging materials on the market. A fabric with an abrasion resistance of 10,000 rubs yields a material with an acceptable level of abrasion resistance for medical and/or sterile packaging Example 3 (Two Pass Laminate)

The degree of thermal consolidation, and hence abrasion resistance/fibre shedding and microbiological filtration performance of a spunbond/meltblown/spunbond laminate can be improved by conducting the initial lamination calendaring step through heated flat steel rollers (as opposed to conventional embossing rollers).

Table 5 below compares the properties of a spunbond/meltblown/spunbond structure laminate made by the standard method (lamination through conventional embossed/flat roll calendar then subsequent flat calendaring of laminate) with the properties of similar laminate made with flat calendar lamination and subsequent flat roller calendaring of the spunbond/meltblown/spunbond structure laminate of an embodiment of the present invention.

TABLE 5

| Process Route | Abrasion Resistance EDANA NWSP 020.5.RO | Fibre Shedding |
|---|---|---|
| Embossed Lamination followed by Flat Calendering of Resultant Laminate | 900 Rubs | Considerable |
| Flat Calender Lamination followed by Flat Calendering of Resultant Laminate | >10,000 Rubs | None |

It has been established the degree of thermal consolidation, and hence abrasion resistance/fibre shedding along with microbiological filtration performance, can be improved by conducting the initial lamination calendaring step through flat bowls (as opposed to conventional embossed roller/flat roller calendar).

It will be appreciated that the embodiments of the present invention herebefore described are given by way of example only, and are not meant to limit the scope of the invention in any way.

It will also be appreciated that the term "medical" used herein is meant to include both human and animal medicine and surgery. It will be further appreciated that any ranges mentioned include within the range the end points of the range.

The invention claimed is:

1. A nonwoven laminate fabric comprising at least three layers comprising spunbond/meltblown/spunbond layers, wherein the laminate fabric has:
    an abrasion resistance of at least 5,000 rubs or higher (as measured by EDANA NWSP 020.5 RO);
    a microbiological filtration performance measured as a log reduction factor (LRF) of 3 or higher (as measured by ASTM F1608); and
    has been flat calendar laminated between flat heated metal rollers; and wherein
    the meltblown layer comprises polymeric fibres comprising polypropylene,
    the fibres of the meltblown layer have an average diameter between 0.5 μm and less than 2 μm, and
    the spunbond layers comprise respective outer layers of the laminate, wherein at least one or each of the spunbond layer(s) comprise polymeric filaments, wherein the filaments of the spunbond layers have a diameter or average diameter less than 19 and at least one of the outer layers is point-bonded or embossed.

2. A nonwoven laminate fabric as claimed in claim 1, wherein the laminate fabric comprises a fabric selected from one or more of: a medical fabric, a pharmaceutical fabric, a medical packaging fabric, a sterile packaging fabric.

3. A nonwoven laminate fabric as claimed in claim 1, wherein the laminate fabric has been calendered and/or laminated without the use of a calendering and/or lamination pattern.

4. A nonwoven laminate fabric as claimed in claim 1, wherein both of the spunbond outer layers are point-bonded or embossed.

5. A nonwoven laminate as claimed in claim 1, wherein the laminate fabric is at least partially permeable and/or transparent to at least one sterilisation means or agents, or at least one of: steam, ethylene oxide (EtO), electrons and gamma radiation.

6. A nonwoven laminate fabric as claimed in claim 1, wherein the layers of the laminate fabric are thermally laminated to one another.

7. A nonwoven laminate fabric as claimed in claim 1, wherein the air permeability of the laminate (measured by the Bendtsen method) is less than 670 ml/min, and/or the air resistance of the laminate material (measured by the Gurley method) is more than 40 s.

8. A nonwoven laminate fabric as claimed in claim 1, wherein the meltblown layer comprises polymeric fibres comprising a single polypropylene homopolymer.

9. A nonwoven laminate fabric as claimed in claim 1, wherein the meltblown layer comprise pores which have a diameter or average diameter in the range of 10 μm to 30 μm (as measured by BS3321).

10. A nonwoven laminate fabric as claimed in claim 1, wherein polymeric filaments of the spunbond layers comprise metallocene polymer/polypropylene or metallocene catalysed polymer/polypropylene.

11. A nonwoven laminate fabric as claimed in claim 1, wherein the laminate fabric has a microbiological filtration performance measured as a log reduction factor (LRF) of 4 or higher, 5 or higher, or 6 or higher.

12. A nonwoven laminate fabric as claimed in claim 1, wherein the laminate fabric has an abrasion resistance of at least 10,000 rubs or higher or around 25,000 rubs.

13. Use of a nonwoven laminate fabric of claim 1, wherein the laminate fabric is used as a component of a medical and/or pharmaceutical product or fabric, such as medical and/or sterile packaging.

14. A method of manufacturing a nonwoven laminate fabric as claimed in claim 1, wherein the method comprises:
  laminating the spunbond/meltblown/spunbond layers together, and
  calendering the laminate with a calendar; wherein
  the calendering of the laminate fabric is done between flat heated metal rollers.

15. The method of claim 14, wherein the laminating of the layers is done between flat heated metal rollers.

\* \* \* \* \*

UNITED STATES PATENT AND TRADEMARK OFFICE
CERTIFICATE OF CORRECTION

PATENT NO. : 11,717,777 B2
APPLICATION NO. : 16/772013
DATED : August 8, 2023
INVENTOR(S) : Avril et al.

It is certified that error appears in the above-identified patent and that said Letters Patent is hereby corrected as shown below:

In the Specification

Column 4, Line 22: Please correct "150l/m$^2$/second" to read --150 l/m$^2$/second--

Column 6, Line 28: Please correct "2600l/m$^2$/second" to read --2600 l/m$^2$/second--

Column 6, Lines 34-35: Please remove the paragraph break between "radiation." and "The spunbond"

Column 10, Line 43: Please correct "150 I/m$^2$/second" to read --150 l/m$^2$/second--

In the Claims

Column 18, Line 42, Claim 1: Please correct "19 and" to read --19 μm, and--

Signed and Sealed this
Twenty-sixth Day of September, 2023

*Katherine Kelly Vidal*
Katherine Kelly Vidal
*Director of the United States Patent and Trademark Office*